United States Patent [19]

Yamabe et al.

[11] 4,116,977
[45] Sep. 26, 1978

[54] PROCESS FOR PRODUCING OXYGEN-CONTAINING CYCLIC FLUORO COMPOUND

[75] Inventors: Masaaki Yamabe, Machida; Kiyotaka Arai, Yokohama; Shunichi Samejima, Tokyo; Makoto Noshiro, Yokohama, all of Japan

[73] Assignee: Asahi Glass Company Ltd., Tokyo, Japan

[21] Appl. No.: 711,978

[22] Filed: Aug. 5, 1976

[30] Foreign Application Priority Data

Aug. 5, 1975 [JP] Japan .................................. 50-94736

[51] Int. Cl.² .................. C07D 307/32; C07D 307/04
[52] U.S. Cl. ................................. 260/343.6; 260/333;
260/343; 260/343.5; 260/345.1; 260/343.9;
260/347.91
[58] Field of Search ..................... 260/333, 343, 343.5,
260/343.6, 345.1, 346.1 R

[56] References Cited

U.S. PATENT DOCUMENTS 2,433,844  1/1948  Hanford .............................. 260/338

OTHER PUBLICATIONS

Kolenko, et al., Tr. Inst. Khim, Ural, Nauchn, Tsentr, Akad. Nauk SSSR 1974, 28, 66-70.

*Primary Examiner*—Cecilia M. S. Jaisle
*Attorney, Agent, or Firm*—Oblon, Fisher, Spivak, McClelland & Maier

[57] ABSTRACT

An oxygen-containing cyclicfluoro compound selected from the group consisting of a perfluorolactone having the formula

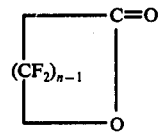

a perfluorocyclic ether having the formula

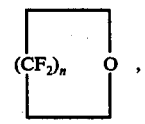

and mixtures thereof is produced by reacting an $\alpha,\omega$-diiodoperfluoroalkane having the formula

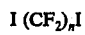

$I(CF_2)_nI$ with fuming sulfuric acid, wherein $n$ is all formulas ranges from 3 to 5.

9 Claims, No Drawings

PROCESS FOR PRODUCING OXYGEN-CONTAINING CYCLIC FLUORO COMPOUND

BACKGROUND OF THE INVENTION

The present invention relates to a process for producing an oxygen-containing cyclic fluoro compound. More particularly, it relates to a process for producing oxygen-containing cyclic fluoro compounds such as fluorine-containing lactones and fluorine-containing cyclic ethers by reacting an α, ω-diiodopolyfluoroalkane with fuming sulfuric acid. Oxygen-containing compounds such as fluorine-containing lactones and fluorine-containing cyclic ethers are useful as intermediates for various fluorine-containing compounds and compounds having special characteristics. For example, the fluorine-containing lactones can be easily converted to the corresponding fluorine-containing dicarboxylic acid derivatives by reaction with a nucleophillic reagent. These derivatives can be effectively used as polybasic acids for producing fluorine-containing condensation polymers such as polyamides and polyesters. On the other hand, the fluorine-containing lactones are intermediates which are useful for the synthesis of various fluorine-containing vinyl monomers, especially fluorine-containing vinyl ethers, and they possess excellent characteristics which enable their use as lubricants, fiber processing agents, and the like. The fluorine-containing cyclic ethers have excellent characteristics as dielectrics and heat transfer media. However, these useful oxygen-containing cyclic fluoro compounds have been hard to produce in high yield. Moreover, the processes necessary for producing these materials are very complicated, and a satisfactory, industrial process for producing these compounds is not known. Thus, for example, fluorine-containing lactones have been produced by heating silver perfluoroglutarate at 125° C. in the presence of iodine (R. E. Banks et al.) However, the yield of the desired perfluoro-γ-butyrolactone compound is only 8% or less (JCS(C) 1967, 2333). In another method of producing fluorine-containing cyclic ethers, an electrolyzing fluorination step has been used as a required step in the process whereby the yield was about 25% or less. This is also quite disadvantageous from an industrial viewpoint. A need, therefore, continues to exist for a method of smoothly and effectively producing useful oxygen-containing cyclic fluoro compounds such as fluorine-containing lactones, e.g. perfluorolactones and fluorine-containing cyclic ethers, e.g. perfluorocylic ethers in high yield.

SUMMARY OF THE INVENTION

Accordingly, one object of the present invention is to provide a process for smoothly producing useful oxygen-containing cyclic fluoro compounds such as perfluorolactones and perfluorocyclic ether in high yield.

This object and other objects of the invention can be attained by reacting an α, ω-diiodopolyfluoroalkane such as 1,4-diiodooctafluorobutane with fuming sulfuric acid to obtain oxygen containing cyclic fluoro compounds.

DETAILED DESCRIPTION OF THE PREFERRED EMBODIMENTS

In the method of the present invention an oxygen-containing cyclic fluoro compound which is a perfluorolactone having the formula

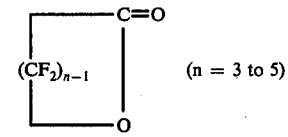

and/or a perfluorocyclic ether having the formula

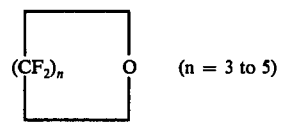

is produced by reacting an α, ω-diiodoperfluoroalkane having the formula $I(CF_2)_nI$ ($n = 3$ to $5$)

with fuming sulfuric acid. In the reaction, suitable α, ω-diiodoperfluoroalkane starting materials of the above formula for the preparation of the oxygen containing cyclic fluoro compounds especially include 1,4-diiodoperfluorobutane. The desired type of oxygen-containing cyclic fluoro compound can be obtained by selecting the appropriate concentration of the fuming sulfuric acid and the appropriate reaction conditions. If an α, ω-diiodoperfluoroalkane having more than 6 carbon atoms is used as a starting material, fluorine-containing dicarboxylic fluorides are mainly produced. On the other hand, if an α, ω-diiodoperfluoroalkane having 3 to 5 carbon atoms is used, cyclic compounds such as perfluorolactones and perfluorocyclic ethers are easily obtained. Moreover, when an α, ω-diiodoperfluoroalkane having 3 to 5 of carbon atoms is reacted with the fuming sulfuric acid, the amount of the perfluorocyclic ether obtained can be increased by increasing the concentration of $SO_3$ in the fuming sulfuric acid whereas the content of the perlfuorolactone can be increased by decreasing the concentration of $SO_3$ in the fuming sulfuric acid. Of course, a mixture of a perfluorolactone and a perfluorocyclic ether can be also obtained as the desired product. If an α, ω-diiodoperfluoroalkane having the formula $I(CF_2)_nI$ ($n = 3$ to $5$)

is used, the principal product is a perfluorolactone. In the reaction of the present invention if an α, ω-diiodoperfluoroalkane starting compound of the formula $I(CF_2)_nI$ wherein $n$ is an integer of 6 to 8 is used, cyclization to an oxygen containing cyclic fluoro compound such as a perfluorolactone or a perfluorocyclic ether hardly occurs, and a perfluorodicarboxylic fluoride is produced as the main product in a yield of about 55 to 60% or more. If the integer $n$ is 5 or less, the yield of the perfluorolactone and the perfluorocyclic ether as the cyclic compounds, is increased while the yield of the perfluorocarboxylic fluoride decreases to about 10 to 15% or less. Accordingly, the kinds of starting materials and the reaction conditions can be selected as desired depending upon the type of oxygen-containing cyclic fluoro compound desired.

In the invention, the α, ω-diiodoperfluoroalkane starting material having the formula $$I(CF_2)_nI$$

can be easily obtained by telomerization using a telogen of $CF_2I_2$, $ICF_2CF_2I$, and a $CF_2=CF_2$ taxogen in the presence of a radical initiator such as benzoyl peroxide. In order to obtain an α, ω-diiodoperfluoroalkane compound wherein n is 3 to 5, from 1 to 2 moles of $CF_2=CF_2$ is reacted with an appropritate amount of telogen. The desired fluoroalkane product is separated from the telomerization reaction mixture by the conventional method.

The concentration of $SO_3$ in the fuming sulfuric acid which is reacted with the α, ω-diiodoperfluoroalkane, is preferably in the range of about 10 to 70% by weight. A catalyst can be used if desired. Suitable catalysts include mercuric sulfate, cadmium sulfate, zinc sulfate, and the like. A small amount of chlorine gas can be added if desired. The reaction of an α, ω-diiodoperfluoroalkane with the fuming sulfuric acid in the process of the invention is not limited and various operational procedures and conditions can be employed. The optimum operating conditions are preferably chosen upon consideration of the kind of starting materials selected as well as the kind of object oxygen-containing cyclic fluoro compound desired and its boiling point. In the reaction, the reaction temperature employed is higher than room temperature, usually in a range of about 30° to 150° C., preferably higher than 50° C., especially in a range of about 60° to 120° C. in order to smoothly conduct the reaction. It is preferable to use an excess of the fuming sulfuric acid based on the $SO_3$ content relative to the α, ω-diiodoperfluoroalkane such as more than 0.1 mole, preferably more than 1.0 mole per one mole of the α, ω-diiodoperfluoralkane compound.

In the actual operational procedure for the reaction, various methods can be employed such as charging the desired amounts of the α, ω-diiodoperfluoroalkane compound and fuming sulfuric acid into a reactor and then heating the contents to a desired temperature. Alternatively, a desired amount of fuming sulfuric acid can be charged into a reactor and then the α, ω-diiodoperfluoroalkane compound is added dropwise to the reactor at a desired temperature to effect the reaction. Another method involves the simultaneous addition of the desired molar ratio fuming sulfuric acid and the diiodo compound to the reactor and subsequent reaction. Still another method involves the dropwise addition of fuming sulfuric acid to the α, ω-diiodoperfluoroalkane compound in the reactor. By these methods the reaction is smoothly and advantageously performed. The reaction time is usually in a range of about 1 to 10 hours, preferably 2 to 6 hours.

In order to obtain a high yield of the cyclic compounds among the oxygen-containing compounds in the invention, it is preferable to use an α, ω-diiodoperfluoroalkane compound having a carbon atom content of less than 5 and to perform the reaction in the presence of $SO_3$, that it, to use an α, ω-diiodoperfluoroalkane compound having the formula $$I(CF_2)_nI \ (n=3 \ to \ 5)$$

and fuming sulfuric acid. When a perfluorolactone is the desired product, it is preferable to use fuming sulfuric acid having an $SO_3$ concentration $SO_3$ of 10 to 15% by weight and if desired, in the presence of a catalyst of zinc sulfate and chlorine. When a perfluorocyclic ether is the desired product, it is preferable to use fuming sulfuric acid having an $SO_3$ concentration greater than 50% by weight. When the concentration of $SO_3$ is less than this value, the content of the perfluorolactone is increased. For example, when fuming sulfuric acid having an $SO_3$ concentration less than 30% by weight is used, the perfluorolactone can be obtained in high yield by reacting excess fuming sulfuric acid based on the $SO_3$ content such as more than 2 moles, preferably 5 to 20 moles, with 1 mole of the α, ω-diiodoperfluoroalkane.

Having generally described this invention, a further understanding can be obtained by reference to certain specific examples which are provided herein for purpose of illustration only and are not intended to be limiting unless otherwise specified.

EXAMPLE 1

Into a four necked flask equipped with a thermometer, a reflux condenser, a dropping funnel and a magnetic stirrer, 4950 g (18.5 moles as $SO_3$) of fuming sulfuric acid containing 30% of $SO_3$ were charged. The flask was heated to 85° C. and then, 990 g (2.2 moles) of 1,4-diiodoperfluorobutane having the forumla I $(CF_2)_4$I were added dropwise to the flask. The reaction was conducted for 6 hours while maintaining the temperature in the reactor at 85° to 95° C. The reaction mixture discharged from the reflux condenser, was passed through a gas washing bottle containing concentrated sulfuric acid and was collected in a flask cooled with a dryice-ethanol coolant. The collected reaction products in the flask were separated by distillation whereby 247 g of a fraction of a boiling point of 18° C. were obtained. According to $F_{19}$ NMR analysis of the fractions, the fraction having a boiling point of 18° C. consisted of 200g (yield of 47%) of perfluoro- γ-butyrolactone and 47 g (yield of 11%) of perfluorosuccinic difluoride. Another fraction having a boiling point of 1° C., 45 g (yield of 11% ) of perfluoroetrahydrofuran was also obtained.

EXAMPLE 2

The process of Example 1 was conducted except that the molar ratio of I$(CF_2)_4$I/$SO_3$ was varied from 1/8.5 to 1/6. The reaction was conducted in the same reactor of Example 1. As a result, perfluoro- γ-butyrolactone was obtained in a yield of 47% together with perfluorotetrahydrofuran (yield of 9%) and perfluorosuccinic difluoride (yield of 10%).

EXAMPLE 3

Into an autoclave, were charged 507 g (1.9 moles as $SO_3$) of fuming sulfuric acid containing 30% of $SO_3$ and 85 g (0.19 mole) of 1,4-diiodoperfluorobutane of the formula $$I(CF_2)_4I.$$

The reaction was conducted at 85° to 95° C. for 1.5 hours. The reaction mixture was collected in a flask cooled in a dry-ice-ethanol bath. Thereafter, it was separated by distillation whereby 12 g (33% yield) of perfluoro- γ-butyrolactone and 3 g (7% yield) of perfluorosuccinic difluoride were obtained as a fraction having a boiling point of 18° C. Another fraction having a boiling point of 1° C., was also obtained. The fraction was 18g (45% yield) of perfluorotetrahydrofuran.

EXAMPLE 4

Into a four necked flask equipped with a thermometer, a reflux condenser, a dropping funnel and a stirrer were charged, 2480 g (18.6 moles as $SO_3$) of fuming sulfuric acid containing 60% $SO_3$. The flask was heated at 60° C., and then 1050 g (2.3 moles) of 1,3-diiodoperfluorbutane $I(CF_2)_4I$ were added dropwise to the contents of the flask. The reaction mixture discharged from the reflux condenser, was passed through a gas washing bottle containing concentrated sulfuric acid and was collected in a flask cooled in a dry-ice-ethanol bath. The collected reaction products in the flask were separated by distillation, whereby 220 g (yield of 45%) of perfluorotetrahydrofuran were obtained as a fraction having a boiling point of 1° C., and perfluoro- γ-butyrolactone (12% yield) and perfluorosuccinic difluoride (6% yield) were obtained as another fraction.

EXAMPLE 5

Into a four necked flask equipped with a thermometer, a reflux condenser and stirrer, 310 g (2.3 moles as $SO_3$) of fuming sulfuric acid containing 60% of $SO_3$ and 105 g (0.23 mole) of 1,4-diiodoperfluorobutane of the formula $I(CF_2)_4I$ were charged and heated. The reaction was conducted while maintaining the reaction temperature of 60° to 70° C. The collection and the separation of the reaction product was conducted in accordance with the process of Example 4. As a result, 23 g (47% yield) of perfluorotetrahydrofuran were obtained as a fraction having a boiling point of 1° C., and perfluoro- γ-butyrolactone (10% yield) and perfluorosuccinic difluoride (5% yield) were obtained as another fraction.

EXAMPLE 6

Into a four necked flask equipped with a thermometer, a reflux condenser, a dropping funnel and a stirrer, 190 g (0.7 mole as $SO_3$) of fuming sulfuric acid containing 30% of $SO_3$ were charged and were heated at 85° C. and then 100 g (0.22 mole) of 1,4-diiodoperfluorobutane having the formula $I(CF_2)_4I$ were added dropwise to the flask. The reaction was conducted while maintaining the temperature in the reactor at 80° to 90° C. The collection and the separation of the product were conducted in accordance with the process of Example 4. As a result, the conversion was 52% and perfluorotetrahydrofuran (62% yield) and perfluoro- γ-butyrolactone (7% yield) were obtained based on the starting material.

EXAMPLE 7

Into a 25 liter glass reactor equipped with a thermometer, a reflux condenser, a dropping funnel and a stirrer, 41 Kg of fuming sulfuric acid containing 30% $SO_3$ were charged and heated at 90° C. Then, 9.15 Kg of 1,4-diiodoperfluorobutane were added dropwise to the flask over 8 hours. The reaction mixture was collected and separated by distillation. As a result, 1.6 Kg (41.0%) of perfluoro- γ-butyrolactone and 445 g (10.2%) of perfluorotetrahydrofuran were obtained.

What is claimed as new and intended to be secured by letters patent is:

1. A process for producing an oxygen containing cyclic fluoro compound selected from the group consisting of a perfluorolactone having the formula

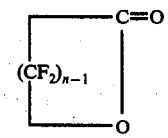

a perfluorocyclic ether having the formula

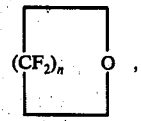

and mixtures thereof which comprises:
reacting an α, ω-diiodoperfluoroalkane compound having the formula $I(CF_2)_nI$ with fuming sulfuric acid, wherein n in wll formulas ranges from 3 to 5.

2. The process of claim 1, wherein the concentration of $SO_3$ in the fuming sulfuric acid is in a range of 10 to 70% by weight.

3. The process of claim 1, wherein the perfluorocyclic ether is principally obtained by employing fuming sulfuric acid having an $SO_3$ concentration greater than 50% by weight as a reactant.

4. The process of claim 1, wherein said perfluorolactone is obtained by employing fuming sulfuric acid having an $SO_3$ concentration of 10 to 50% by weight as a reactant.

5. The process of claim 1, wherein excess fuming sulfuric acid is employed as a reactant in which the concentration of $SO_3$ is said fuming sulfuric acid amounts to more than 2 moles of $SO_3$ per mole of α, ω-diiodoperfluoroalkane.

6. The process of claim 1, wherein a catalyst of mercuric sulfate, cadmium sulfate or zinc sulfate is used in the reaction.

7. The process of claim 6, wherein a small amount of chlorine is added to the reaction.

8. The process of claim 1, wherein the reaction temperature is in a range of 30° to 145° C.

9. The process of claim 1, wherein said α, ω-diiodoperfluoroalkane is 1,4-diiodoperfluorobutane.

* * * * *